(12) United States Patent
Franzen

(10) Patent No.: US 6,428,987 B2
(45) Date of Patent: Aug. 6, 2002

(54) DEVICES FOR FAST DNA REPLICATION BY POLYMERASE CHAIN REACTIONS (PCR)

(75) Inventor: Jochen Franzen, Bremen (DE)

(73) Assignee: Bruker Daltonik GmbH, Bremen (DE)

( * ) Notice: Subject to any disclaimer, the term of this patent is extended or adjusted under 35 U.S.C. 154(b) by 0 days.

(21) Appl. No.: 09/735,372

(22) Filed: Dec. 12, 2000

Related U.S. Application Data

(62) Division of application No. 09/049,646, filed on Mar. 27, 1998, now Pat. No. 6,180,372.

(30) Foreign Application Priority Data

Apr. 23, 1997 (DE) .......................................... 197 17 085

(51) Int. Cl.[7] .......................... B01J 10/00; G01N 15/06; G01N 21/00; C12P 15/64
(52) U.S. Cl. ...................... 435/91.2; 422/196; 422/197; 422/68.1; 422/57; 422/81.12; 435/290; 435/316
(58) Field of Search ................................. 435/912, 290, 435/316; 422/196, 197, 68.1, 57, 81.12

(56) References Cited

U.S. PATENT DOCUMENTS

| | | | |
|---|---|---|---|
| 5,120,662 A | 6/1992 | Chan et al. | |
| 5,176,203 A | 1/1993 | Larzul | |
| 5,498,392 A | 3/1996 | Wilding et al. | |
| 5,720,923 A | * 2/1998 | Haff et al. | 435/68.1 |
| 5,849,208 A | 12/1998 | Hayes et al. | |

FOREIGN PATENT DOCUMENTS

| | | |
|---|---|---|
| EP | 0636413 A2 | 2/1995 |
| FR | 2672231 | 8/1992 |
| WO | WO 9213967 | 8/1992 |

OTHER PUBLICATIONS

Adam T. Woolley et al., Anal. Chem. 1996, 68, Functional Integration of PCR Amplification and Capillary Electrophoresis in a Microfabricated DNA Analysis Device, pp. 4081–4086.
Burke et al., Genome Research, Microfabrication Technologies for Integrated Nucleic Acid Analysis, 1997 by Cold Spring Harbor Laboratory Press ISSN 1054–9803/97, pp. 189–197.
Swerdlow et al., Anal. Chem., vol. 69, No. 5, Mar. 1, 1997, Fully Automated DNA Reaction and Analysis in a Fluidic Capillary Instrument, pp. 848–855.
Nakano et al., Biosci. Biotech. Biochem., 58 (2) 1994, High Speed Polymerase Chain Reaction in Constant Flow, pp. 349–352.

* cited by examiner

*Primary Examiner*—Gary Benzion
*Assistant Examiner*—Joyce Tung

(57) ABSTRACT

The invention concerns instruments for fast, selective replication of deoxyribonucleic acid (DNA) from biomaterial through polymerase chain reaction (PCR), working in individual duplication thermocycles. The invention consists of extremely brief cycle times of only a few seconds for the PCR reactions, generated, on the one hand, by reaction chambers for the reception of the reaction solution constructed of a pattern of fine capillaries in close proximity to heating and cooling elements in order to optimally accelerate the temperature setting in the reaction solution for the three temperature phases of the PCR duplication cycles and, on the other hand, by keeping the flow rates in the capillaries to a minimum during the amplification phase so that the polymerase reaction is not disturbed. The capillary pattern can be simply produced by means of microsystem technology.

22 Claims, 3 Drawing Sheets

DEVICES FOR FAST DNA REPLICATION BY POLYMERASE CHAIN REACTIONS (PCR)

CROSS REFERENCE TO RELATED APPLICATIONS

This is a divisional of U.S. patent application Ser. No. 09/049,646, filed Mar. 27, 1998 now U.S. Pat. No. 6,180,372.

FIELD OF THE INVENTION

The invention concerns instruments for fast, selective replication of deoxyribonucleic acid (DNA) from biomaterial by the well-known polymerase chain reaction (PCR), working in individual duplication thermocycles.

DESCRIPTION OF THE RELATED ART

It is becoming more and more important for the medical care of patients that analysis methods in genetic engineering are made available which work very quickly. One example of this is the identification of infectious microorganisms, which still requires days at present, but actually requires treatment at the earliest possible stage, in the initial hours if possible. More intense will be the demand for quick analysis during examinations of tissue possibly affected by cancer or other disease during surgery on the open patient by means of oncogenetic, virological or bacteriological analyses. Here, a maximum analysis time of about ten minutes is required.

Mass spectrometry today provides very fast, highly sensitive analysis methods for the size of amplified DNA segments. Advances in matrix-assisted laser desorption and ionization (MALDI) make it possible to analyze about 20 samples including the MALDI preparation, the introduction of DNA MALDI samples into the mass spectrometer, the MALDI analysis and the data evaluation up to presentation on the screen in less than three minutes. The tissue cells and DNA extraction can be lysed in less than two minutes.

This maximum of five minutes total for sample preparation and mass spectrometry analysis stands in contrast to times of three hours for classic PCR replication. Extreme reductions in these times are on the horizon however. In one instrument, available commercially in the meantime, this time has already been reduced to about 20 minutes. In a recent publication (A. T. Woolley et al., "Functional Integration of PCR Amplification and Capillary Electrophoresis in a Microfabricated DNA Analysis Device", Anal. Chem. 68, 4081, December 1996), DNA in 20 microliters of reaction solution was amplified through 30 cycles in only 15 minutes in a miniature chamber made of polypropylene. Even this time is, however, too long for a fast analysis in the above sense. The goal must be to perform the PCR amplification in only two to three minutes.

As is known, DNA consists of two complementary chains made up of four nucleotides, the sequence of which forms the genetic code. Each nucleotide consists of a sugar (ribose), a phosphoric acid group and a base. Two bases each are complementary to one another. Sugar and phosphoric acid form the continuous chain of the DNA (or the so-called backbone), the four characteristic bases are each lateral branches attached to the sugar. Both complementary chains or single strands of DNA are coiled around one another in the form of a double helix, whereby two complementary nucleotides each are connected to one another via hydrogen bridges between the bases and thus form a so-called double strand.

The basis for many analysis methods in genetics is the selectively functioning PCR (polymerase chain reaction), a simple replication method for specifically selected DNA pieces in a test tube, first developed in 1983 by K. B. Mullis (who received the Nobel Prize for this in 1993) and which, after the introduction of temperature stable polymerases, went on to unequalled success in genetic engineering laboratories.

PCR is the specific replication of a relatively short segment of double-stranded DNA, precisely sought from the genome, in simple temperature cycles. Selection of the DNA segment is through a so-called pair of primers, two DNA pieces with about 20 bases length apiece, which (described somewhat briefly and simply) encode the bilateral ends of the selected DNA segment. Replication is performed by an enzyme called polymerase, which represents a chemical factory in a molecule. The PCR reaction takes place in aqueous solution in which a few molecules of the original DNA and sufficient quantities of polymerase, primers, triphosphates of the four nucleic acids (so-called "substrates"), activators and stabilizers are present. In every thermal cycle, the DNA double helix is first "melted" at about 95° C., whereby both strands are separated from one another. At about 55° C., the primers are then attached to complementary nucleotide sequences of the DNA single strands ("hybridization"). At 72° C. the double helixes are reconstructed by elongation of the primers, done by the temperature-resistant polymerase (e.g. taq-polymerase). Complementary nucleotides are bonded, one after the other, to a specific end of the primers to form two new double helixes. In this way, the selected DNA segment is duplicated in principle between the primers. Therefore, over 30 cycles, around one billion DNA segments are generated from one single double-strand of DNA as original material. (In a more exact description, the shortening to the DNA segment between the primers only occurs statistically with further replications).

The duration of time for a thermal cycle is practically only dependent on the rate of heating up and cooling down, which is subsequently dependent upon the volume of liquid, the dimensions of the chamber and the thermal conductivity of the chamber walls and the reaction solution. For every thermal stage, only a few seconds are necessary in principle, sometimes even less.

In the above cited article by Woolley et al., in which the PCR amplification for 30 cycles only lasted 15 minutes, the following times were required, for example, for the work in the three thermal stages: 2 seconds at 96° C. for melting, 5 seconds at 55° C. for the primer attachment and 2 seconds at 72° C. for reconstruction. The remaining time of 21 seconds per cycle was used for the thermal transitions. The DNA melts almost instantaneously at a temperature a few degrees above the "melting temperature." Analyses have shown that heating to this temperature for one half second suffices for complete separation of all double helix structures. Precise maintenance of the temperature is not even especially critical here, as long as one remains above the melting temperature but below a coagulation temperature. Hybridization also does not need much time if the primers are available in sufficient concentration. At an optimal concentration, about one to two seconds are enough. For hybridization, the temperature is even less critical; it need only remain under 60° C. to proceed sufficiently fast. Optimal conditions are at about 55° C.

The growth of the attached primers into a complementary DNA molecule through the polymerase, known as "reconstruction" in the following, has a very high velocity. 500 to 1,000 bases can be bonded per second under optimal thermal and concentration conditions by the polymerase. Since generally only DNA segments of a maximum of 400 bases in length are necessary for the analyses, two seconds are quite sufficient for this reconstruction phase. For this process of reconstruction of a new double helix, good maintenance of the optimal temperature is required in order to achieve the high rate of reconstruction.

Theoretically, a PCR reaction cycle could thus be concluded in less than 5 seconds, under the precondition that heat can be introduced or removed up to each sufficient thermal equilibrium in about ¼ second each. One such ideal thermal curve for a PCR cycle is shown in FIG. 1. The introduction and removal of heat are the critical time-determining variables here.

By the addition of only one primer pair, uniform DNA segments can be replicated. However, if several different primer pairs are added at the same time, several DNA segments will also be replicated at the same time ("multiplexed PCR"). This type of multiplexed PCR is frequently used and often has special advantages. For so-called "fingerprinting" for the identification of individuals through DNA segments of variable length (methods of "VNTR=Variable Number of Tandem Repeats" or "AMP-FLP=Amplified Fragment Length Polymorphism"), it makes the analyses faster. Here through the selection of primers, which determines the average molecular weight of the DNA segments, the result can be achieved that the variations of molecular weights for the DNA segments formed by the various primer pairs only seldomly or never overlap. This type of multiplexed PCR requires an analyzer which is capable of simultaneous measurement of a large range of molecular weights. The method is particularly advantageous for the identification of infectious organisms, since 20 types of bacteria (or viruses, yeasts, molds) can be detected at the same time, for example, with a single PCR replication.

The high sensitivity of modern measurement methods for the analysis of DNA, for example the sensitivity of the above-mentioned mass spectrometric measurements, permits the volume of reaction solution to be reduced while maintaining the optimal concentration. Since on the one hand, for the same initial amount of DNA, the reaction solution is then exhausted after a few cycles (though on the other hand not very much amplified DNA material is required for the analysis) the number of cycles can be reduced from the normal amount of 30 to about 24 to 28. However, the time-saving due to this is minimal. Possible reduction of the volumes suggests a solution based on microfabrication technologies for a new PCR amplification method such as has already been applied in the above cited article by Woolley et al.

Also in the review article "Microfabrication Technologies for Integrated Nucleic Acid", D. T. Burke, M. A. Burns and C. Mastrangelo, Genome Research 7, 189 (1997), chambers manufactured using microfabrication technology are presented for PCR amplification, without however giving any indication of the achievable rates. Such chambers, 1,000× 1,000×250 micrometers large here and made of a low temperature polymer, nevertheless have the disadvantage that they can only be emptied by extended rinsing with a washing liquid and thus force a dilution of the amplified DNA when emptying.

Another obvious idea is to allow the reaction solution to run constantly through a fine capillary which crosses three zones, kept stationarily at the appropriate temperatures, on a microfabricated chip in a simple manner for every cycle, whereby the standard temporal variation in the temperature is replaced by a simple local variation in temperature. A section of one such arrangement is shown in FIG. 3. A small dimension for the capillary should then allow a rapid temperature change up to thermal equilibrium.

Unfortunately, the flow in a capillary impairs the work of the polymerase in the reconstruction phase. In a cylindrical capillary, a laminar flow with a parabolic velocity profile generally prevails, whereby the average velocity is doubled in the central axis of the capillary while it is zero at the margin of the capillary. In a capillary with a square or rectangular cross section, somewhat different conditions prevail, however the differences are not decisive here. The flowing reaction solution is therefore divided into sliding layers of differing velocity, while adjacent molecules in different sliding layers move past one another. The individual molecules are subject to shearing forces. Straight molecules are aligned parallel to the direction of flow. For a close-to-real average velocity of 2 millimeters per second in a capillary 100 micrometers in diameter, two almost spherical molecules which are in contact with one another on both sides of an imaginary sliding surface, move past one another in one millisecond by about 8% of their diameter on average. One millisecond corresponds to the minimum time for the incorporation of a base. Molecules in the center of the flow do not experience this sort of displacement. Molecules close to the wall of the capillary experience a greater displacement. In this way, however, the work of the polymerase which requires a calm, adjacent positioning of the molecules on a millisecond scale, is greatly impaired. Increased errors are the result and, with even greater displacement motion, the polymerase work is even stopped. The displacement motion of adjacent molecules increases for the same flow in proportion to the third power of the reciprocal diameter of the capillary. There is therefore a dilemma for the flow PCR: thinner capillaries improve the temperature setting, however they extend the distance, therefore necessitating an increased flow rate and thus impairing amplification.

SUMMARY OF THE INVENTION

The invention makes use of extremely brief cycle times of only a few seconds for the PCR reactions. These reaction are generated by using PCR reaction chambers constructed as a pattern of fine capillaries in close proximity to heating and cooling elements, and by keeping the flow rates in the capillaries to a minimum during the amplification phase so that the polymerase reaction is not disturbed. In this way, the temperature cycles in the reaction solution for the three temperature phases of the PCR duplication can be optimally shortened in duration. The capillary pattern can be simply produced by means of microfabrication technology.

It is the basic idea of the invention to use, on the one hand, a pattern of very fine capillaries in close proximity to heating and cooling elements as a chamber system for the reaction solution in order to keep the heating and cooling-down times for the reaction solution extremely low, while on the other hand however keeping the flow rate for the reaction solution in the capillaries during the reconstruction phase of the DNA double strand using the polymerase as low as possible. The flow rate during the reconstruction phase should never exceed ten times the maximum capillary diameter prevalent there per second, while more favorable would be a medium flow rate of less than five maximum capillary diameters per second. The error rate for the reconstruction only approaches its minimum below a medium flow rate which is less than double the diameter per second. The maximum capillary diameter corresponds to the normal diameter for round capillaries, for rectangular cross sections that of the diagonal.

A favorable, very fine capillary structure with closely adjacent heating elements may be favorably produced using microfabrication technologies. The low flow rate can be provided on the one hand (especially at a constant flow of reaction solution through the capillary structure) by a special design of the capillary net, on the other hand, the low flow rate may also be produced by special methods of application with temporally changeable flows of the reaction solution.

The advantage of a fine capillary structure is evident: the times for the thermal transitions in the reaction solution may be kept very short. This advantage is however opposed by severe disadvantages: the extremely large surface area of the chamber system disturbs the biochemical processes if the surface even only minimally influences the affected molecules. Thus for example a bare silicon surface immediately kills the activity of the polymerase. Many plastics too have proven to be unsuitable for the PCR. Even the same plastics from different manufacturers, for example the normally favorable plastics polyethylene or polypropylene, have had different types of effects on the PCR due to their varying qualities. Therefore, the surface must very thoroughly be made completely inert.

The activity of a surface can be almost completely eliminated by a thorough coating. Coating methods for capillaries are known from chromatography, especially from gas chromatography, which eliminate even the smallest remnant of active surface. Particularly coatings with thread-shaped molecules which are bonded monolaterally onto the surface ("chemically bonded phases"), have generated thermally stable and extremely inert surface coatings. Here, hydrophobic or hydrophilic, polar or nonpolar, fat or water absorbent surface coatings can be generated which may also have other characteristics within the depth of the layer. It is therefore a further idea of the invention to use the known chromatographic coatings for the deactivation of surfaces. Particularly for the coating of quartz glass and glass surfaces on the interior of thin capillaries, explicit and comprehensive formulas with descriptions of the necessary steps are available. Silicon surfaces can be transformed by oxidation into quartz surfaces.

Particularly for metal implants, stable coatings have been developed which correspond to endogenous proteins and glycoproteins such as occur in cell membranes. Such coatings may reduce the activities on the surfaces for polymerase reactions in the present case, even if they are not yet successful as implant coatings. The micromanufacturing methods, however, also comprise the molding of plastics in micromanufactured silicon forms. In this way as well, capillary systems can be developed which may be used as reaction chambers. It is therefore a further idea of the invention to use favorable polymers such as low pressure polyethylene or polypropylene for the manufacture of capillary systems. Since polymers normally possess poor thermal conductivity characteristics, these may also be filled with thermally well conducting nanopowders, for example with silver powder. These powders can be produced with a particle diameter of about 10 to 1,000 nanometers. They are excellently suited for increasing the thermal conductivity of plastics. The powders may be deposited in such a way that they do not directly lie on the surface. The low flow rate necessary for this invention can be achieved in a constantly circulating capillary system, whereby zones of different temperatures are passed through, in such a way that the flow of the reaction solution in the zone of reconstruction temperature branches off into a multitude of parallel capillaries, in which the flow rate in each of these parallel capillaries is reduced as shown in FIG. 4.

The reaction solution can also be moved on intermittently by pressure pulses. After each filling of the capillary system for the reconstruction of the DNA double strand, at the corresponding temperature, the flow of the reaction solution stops, the incorporation reactions run down and only then (after about 2 seconds) is the reaction solution pumped on. It is therefore advantageous to keep each of the volumes at equal amounts for the chamber systems for melting, attachment of primers, and reconstruction, so that the reaction solution is always pressed on by exactly this amount of volume. A pulsed process occurs which, however, makes it imperative for the dwell times of the reaction solution to be equal in the three temperature zones.

It is however also possible, in particular, to select a capillary system large enough so that the entire quantity of reaction solution to be processed can be held in it and then very quickly passed through the temperature phases one after another using fast heating and cooling elements with the solution at rest.

Such a type of capillary system may easily be aligned in one plane, as shown in FIGS. 2a and 2b. The capillaries arranged in a plane are enclosed in a thin membrane, on the surface of which there are heating elements, also in a planar structure. Thus for example, 200 nanoliters of reaction solution in 16 parallel capillaries with cross sections of 60×100 micrometers and 2 millimeters length can be located on a surface of about 2×1.6 millimeters. These capillaries are located in a silicon membrane of 300 micrometers maximum thickness. Through the thin membrane and through the bridges between the capillaries, heat can be applied or discharged very efficiently.

On the top and bottom of the membrane, there are resistance grids planarly imbedded or otherwise attached, which take care of the heating capacity. With less than two watts heating capacity, the temperature of this type of thin silicon membrane with a surface of 3×3 $mm^2$ can be raised by about 100° C. per second, an increase from 45° C. to about 72° C. can therefore be achieved in 0.3 seconds. The temperature can itself be determined in the known fashion via the thermal coefficient from the resistance of the heating element. Control of the heating capacity with a slight overshoot leads to quick adjustment of the equilibrium in the reaction solution. Via gaseous, liquid or solid movable cooling means, which can be brought into planar contact with the membrane the membrane can be cooled very quickly. An arrangement with a solid cooling element is depicted in FIG. 2b. In the simplest case, the cooling means may be at room temperature, or at a lower temperature for acceleration. Since the temperature for primer attachment need not be exactly adjusted, a simple time control is sufficient for the contact time. In more critical cases, the change in resistance for the heating elements may be exploited as a control of the contact time. The cooling means, moved for example electromechanically or pneumatically, may be a part of the microsystem arrangement, or they may also be brought in contact with the membrane through external movement devices.

BRIEF DESCRIPTION OF THE DRAWINGS

FIG. 2a shows the capillary structure with inlet channel (1), flow distributor (2) for uniform filling of the parallel capillaries, parallel capillaries (3), flow collector (4) and outlet channel (5). FIG. 2b shows a cross section through the membrane (6) with the parallel capillaries, the heating elements (7,8) and the movable solid cooling elements (9,10).

FIG. 3 shows an unfavorable arrangement for this capillary structure since the flow rate is equal for all thermal levels.

DETAILED DESCRIPTION OF THE PREFERRED EMBODIMENTS

Figure 3:
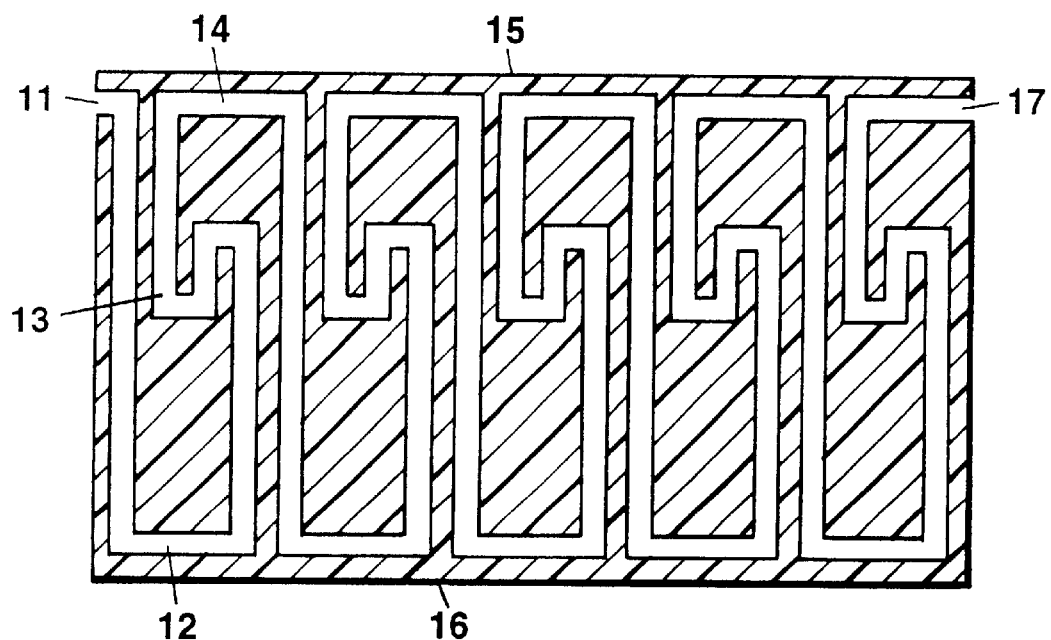
FIG. 3 shows the principle of an (unfavorable) capillary arrangement in which the reaction solution in the capillary flows through three places of varying temperature per cycle. The upper edge (15) of this structure is in contact with a heater which keeps the edge at about 100° C., while the lower edge (16) is kept at about 50° C. through cooling. After flowing through the melting region (11) at about 95° C., the reaction solution flows to the opposite edge and is cooled in a primer attachment region (12) to about 55° C. Then it flows to a reconstruction region (13) in which it is heated to about 72° C. This area has a somewhat longer flow-through path to achieve a somewhat longer time for the reconstruction phase. From there the reaction solution flows into the next melting region (14) which belongs to the next temperature cycle.

It seems expedient to generate a capillary structure in a silicon chip by microfabrication techniques with stationary thermal distribution as shown and described in FIG. 3, and to have the reaction solution flow through it at a constant rate. It however appears that the PCR reaction at capillary diameters below about 400 micrometers are considerably disturbed by the necessarily high flow rate in the capillaries. However this capillary diameter is still much too great for the heating rates required here. On the other hand, in order to maintain the polymerase work at the usual low error rate of $10^{-4}$, a flow rate is necessary that is so low that no substantial reduction in total time is achieved.

Figure 4:
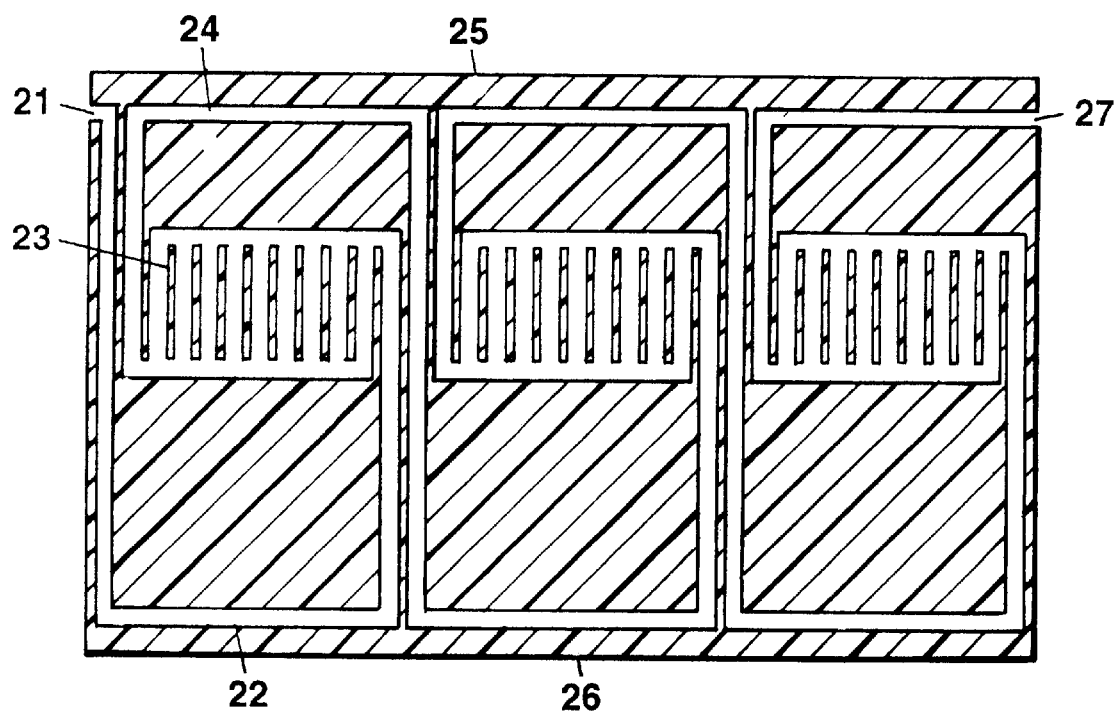
FIG. 4 shows a more favorable embodiment of a capillary arrangement for constant flow. In the reconstruction region (23) the capillary branches off into a number of parallel capillaries with equal cross sections, which greatly reduces the flow rate here. Otherwise this arrangement is equal in all parts to the arrangement in FIG. 3.

One embodiment greatly improved by the idea of the invention is therefore provided by a capillary structure on a chip as shown in FIG. 4. Here the capillary branches off without constrictions in the reconstruction region. In this way, a reduction in flow speed for PCR amplification may be achieved. It is an advantage of this arrangement that, due to the continuous operation in this structure, alternating quantities of reaction solution may be subjected to PCR amplification, although the time advantage disappears.

This chip structure also has disadvantages, however. It is relatively long and narrow (about 4×60 millimeters), unusual for a microfabricated chip and very fragile, and it is additionally subject to strong thermal stress. These disadvantages may be partially balanced out by a circular or loop-shaped arrangement with central heating, or by a convoluted arrangement with capillary levels lying on top of one another, which leads to a reduction in the overall structure. A further disadvantage is the fixation of the number of PCR cycles, strictly prescribed by the number of structure repetitions in the microfabricated chip. Another disadvantage is the relatively long duration of the overall process including emptying after the work has already been completed for the front of the reaction solution passing through.

It is therefore advantageous to fill a larger volume pattern with very fine capillaries only once, to allow the PCR reactions in the reaction solution at rest to run through temporal thermal cycles and then empty the structure again once.

In principle, this type of operation may be performed in a single, multiply convoluted, continuous capillary, however the process of filling and emptying is then relatively long. Filling and emptying times are not insignificant. For example, a capillary with a cross section of 100×60 micrometers, which should hold about 250 nanoliters, is already over 40 millimeters long and requires 40 seconds already for these processes at a filling and emptying rate of 2 millimeters per second. If still other processing steps are included, the filling and emptying times become prohibitively long.

Figure 1:
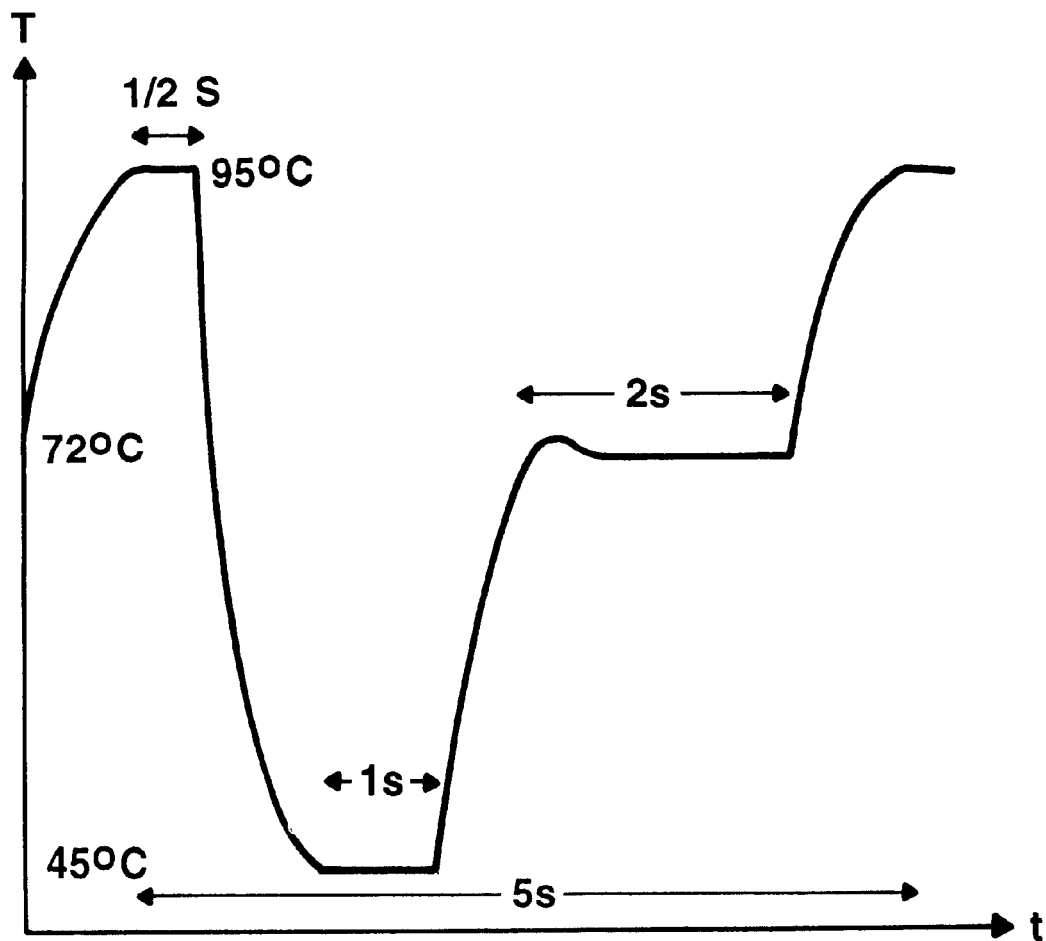
FIG. 1 shows a cycle of an optimal thermal profile, unobtainable previously without this invention, for fast DNA amplification by PCR. The three thermal levels of the cycles are run through in only 5 seconds. A DNA amplification with 30 thermal cycles therefore takes only 2½ minutes.
Figure 2B:
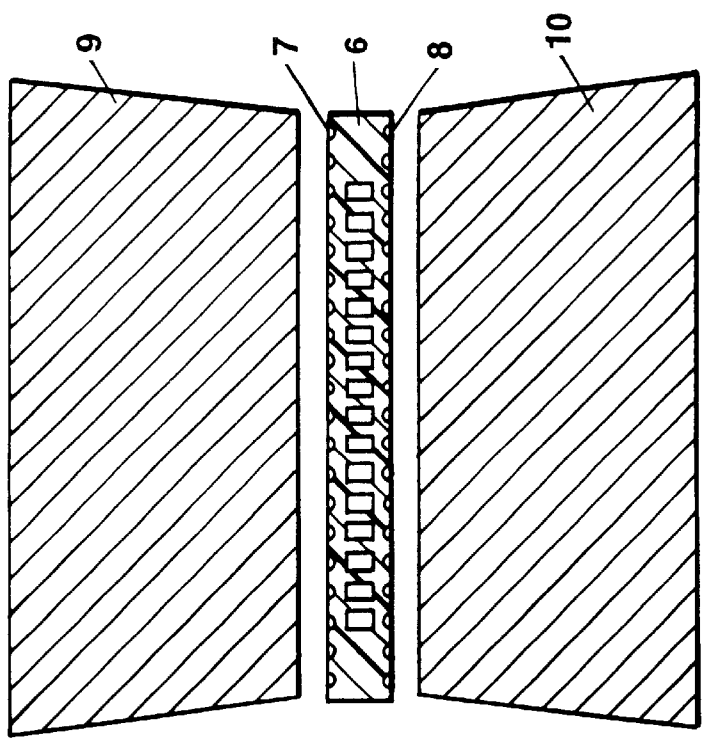
FIGS. 2a and 2b show a microfabricated membrane for DNA amplification with the reaction solution at rest.
Figure 2A:
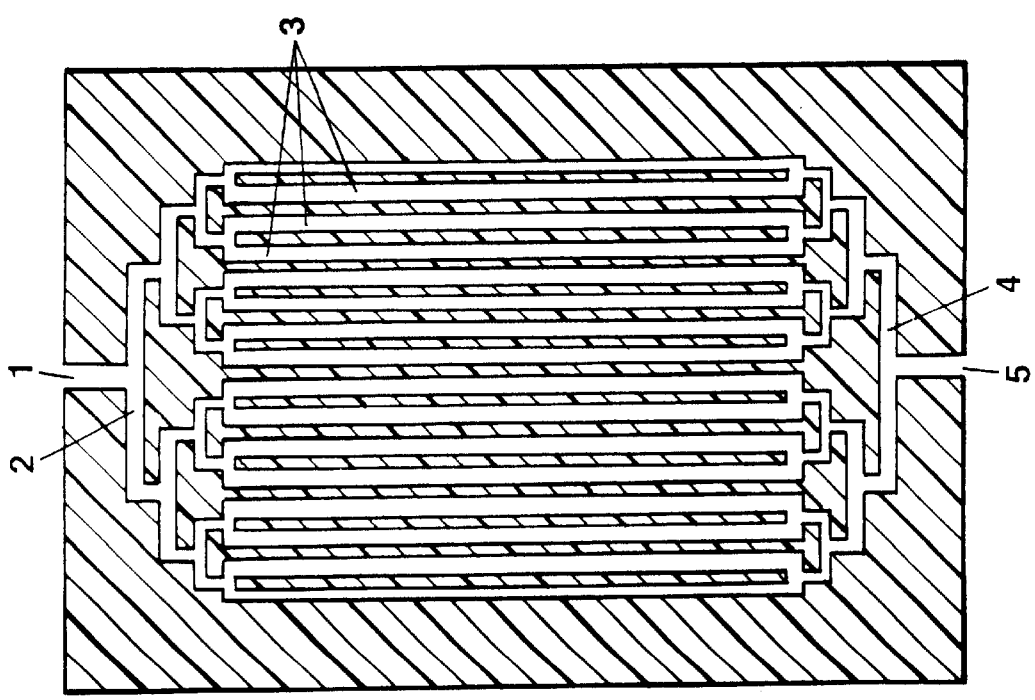

A particularly favorable embodiment is therefore shown in FIGS. 2a and 2b. This is a number of parallel capillaries (3) which lie in the central level of a thin, microfabricated membrane (6). Two distributor systems (2,4) at the start and end of the parallel capillaries, which guarantee equal flow resistances for all inlet and outlet ways of the parallel capillaries, ensure a strictly cophasal filling. This capillary structure is filled at the beginning of PCR amplification, afterwards the reaction solution is at rest. The heating elements (7, 8) on the surface of the membrane can heat up the membrane and, with it, the reaction solution in a very brief time. Thus 2 watts of heating capacity suffice in order to generate a temperature increase of more than 100° C. per second. The increases from the primer attachment temperature (55° C.) to reconstruction temperature (72° C.) and then to melting temperature (95° C.) may be passed through in about ¼ second each. If the heaters are operated, for example, by a high frequency alternating current, the thermal coefficients may then be used in the known fashion to measure the temperature in the heater and thus control the heating process.

The membrane is cooled in this embodiment via two gold or silver-plated elements made of copper (9, 10), which are pressed against the membrane by an electromechanically or pneumatically generated movement, producing a large area thermal contact. A mechanical forced coupling of the opposing movements of both cooling elements can protect the membrane from damage. The cooling outlets are provided with cooling vanes cooled using ambient air.

For strong cooling, a simple air or water cooling system may also be considered. An air system is especially advantageous because the air may serve as an thermal isolator as soon as the air flow stops. The thermal discharge of the thin membrane then takes place in less than half a second.

If the parallel capillaries are filled, at the beginning of the PCR process, with a very few DNA double strangs only, it may happen that only one or two capillaries contain amplifyable DNA. In this case, the complete reaction solution may be drawn back after some initial PCR cycles, mixed, and returned into the capillary system to have a better distribution among the capillaries.

After completing the PCR amplification, the capillary structure is emptied by washing liquid forced from behind. The DNA solution is cleaned by well-known means and transferred to analysis. The capillary structure is washed out sufficiently well and is once again available for the next PCR amplification.

This capillary structure in a microfabricated membrane does not allow any change in volume of the process reaction solution. Since for this type of analysis firm amounts of DNA are required, this is not a serious disadvantage. In contrast to this, this structure allows alternating numbers of replication cycles. In this way DNA amplification may be adapted in an advantageous manner to the amount of DNA in the original materials. If the DNA from only a few cells (about 100) is available, 32 cycles may be run, for example, or if on the other hand, the DNA is from several thousand or even tens of thousands of cells, 24 cycles may suffice. Therefore, this type of temporal variation of temperature is more flexible than the above described variations of reaction solution flowing through areas of differing temperature.

The initial cycles may, in this type of device, also run more slowly in order to ease the hybridization, and if enough short DNA segments are generated, the rate can be increased. It should be mentioned, however, that the number of DNA sets at the beginning should not be much below 100 DNA sets, because all of the parallel capillaries must be filled with an appropriate number of DNA sets to be effective amplifiers.

Analysis of amplified DNA segments may for example proceed mass spectrometrically through ionization using matrix-assisted laser desorption (MALDI) in a time-of-flight mass spectrometer (TOF). To do this, the DNA is applied together with suitable matrix substances onto a sample support. The MALDI sample supports are then introduced in a known manner into the ion source of the mass spectrometer and the individual DNA sample substances are automatically measured for the molecular weights of the DNA substance in an equally known fashion. Electrospray ionization with ion trap mass spectrometers, using well-known nanospray methods, constitutes an alternative method of analysis.

All of the above described capillary systems require deactivation of the inner capillary surfaces so that the polymerase work is not disturbed. Experiments have shown that bare silicon surfaces inactivate the polymerase immediately.

The inner capillary surfaces must therefore be coated with deactivating layers. Very good coating methods for deactivation are known from capillary gas chromatography. The glass or quartz glass capillaries used there also have very active surfaces, in this case active in adsorbing substances. The activity essentially proceeds from free OH groups. Such free OH groups are also responsible for the disturbance of the polymerase.

For capillary gas chromatography, various coating substances have been developed. Since these substances form the liquid phase of this type of distribution chromatography (which is often called GLC=gas-liquid-chromatography instead of just GC), the coating substances are simply called "phases" here. There are polar and nonpolar phases, hydrophilic and hydrophobic. For well over 20 years, so-called "chemically bonded phases" have established themselves in which long, thread-shaped molecules are bonded chemically covalently on the surface, side-by-side like seaweed. These phases are thermally stable up to several hundred degrees Celsius and long-lasting.

Due to the parallel arrangement of the phase molecules, any desired arrangement can be custom-tailored here. Thus a superficially hydrophobic layer may be made hydrophilic on the inside. The thickness can be adapted to the requirements. Silicon rubber phases are primarily used standard phases in gas chromatography, however they are less favorable for PCR reactions, while on the other hand waxy phases are better, for example Carbowax.

In the future, coatings with biomaterials such as proteins, lipid proteins or glycoproteins will play a greater role as coating materials. It is already possible to bind such molecules covalently onto the surfaces of metals. It can be expected that these biomaterial coatings will be even more favorable for deactivation of the surfaces for polymerase work.

However, it is also possible to generate the capillary system of polymer plastics using microfabrication methods and tools. Microprinting processes exist which proceed from a silicone structure as a matrix. Using known microwelding or microadhesion techniques, the production of thin membranes with imbedded capillaries is also possible. The finished membranes may be printed with a resistance network; such resistance networks can be created by applying metal layers and then etching. Plastics may be filled with metallic powders to improve the thermal conductivity, such as with silver nanopowder.

The methods and structures described may of course be varied in many ways. It is simple for a specialist, following the indicated invention ideas, to develop further capillary structures and other operating methods.

Thus it is possible, for example, to replicate and finally to analyze RNA in the above described fashion as DNA after a first duplication step using "inverse transcriptase", which reconverts the RNA back into a DNA complementary sequence. This process, too, may be performed in a unified, microfabricated apparatus. Extensive changes or derivations of DNA toward the goal of achieving more easily analyzable output products for analysis may also be performed in instruments especially adapted for this, produced using microfabrication technologies.

What is claimed is:

1. Apparatus for use in replicating DNA located in a polymerase chain reaction (PCR) fluid, the apparatus comprising:

a housing having a flow path through which the reaction fluid may flow, the flow path including a set of reaction chambers comprising a plurality of capillaries into which fluid flowing through the flow path is divided to flow simultaneously before being recombined, such that a flow rate of the reaction solution through the parallel capillaries is lower than elsewhere in the flow path; and heating apparatus that provides heat to the flow path such that at least three different temperatures affect the reaction solution, the solution being subjected to at least one of the three temperatures while simultaneously present in the capillaries.

2. Apparatus according to claim 1, wherein the capillaries each have a diameter below 400 micrometers.

3. Apparatus according to claim 1, wherein the volume of each reaction chamber is less than one microliter.

4. Apparatus according to claim 1, wherein the capillary reaction chambers are each microfabricated from silicon, and the surface of the capillaries is coated with a coating material that does not inhibit PCR.

5. Apparatus according to claim 4, wherein the coating material has been bonded chemically to a surface of the silicon.

6. Apparatus according to claim 4, wherein the coating material comprises a chromatographic coating.

7. Apparatus according to claim 4, wherein the coating material comprises nonpolar phase Carbowax.

8. Apparatus according to claim 4, wherein the coating material comprises glycoproteins, proteins or lipoproteins.

9. Apparatus according to claim 1, wherein the capillaries comprise polymer plastics.

10. Apparatus according to claim 1, wherein the capillaries comprise polyethylene or polypropylene.

11. Apparatus according to claim 1, wherein capillaries comprise, at least in part, a material with a high thermal conductivity.

12. Apparatus according to claim 1 wherein the three temperatures correspond to temperatures appropriate for the phases of PCR melting, primer attachment and reconstruction.

13. Apparatus according to claim 12 wherein a reaction solution passing through the flow path is at the reconstruction temperature while in the capillaries.

14. Apparatus according to claim 1 wherein the heating apparatus comprises fluid cooling means that can be brought into thermal contact with the capillaries to change the temperature of the reaction solution in the capillaries.

15. Apparatus according to claim 1 wherein the flow rate through the capillaries is no greater than a value equal to ten times the diameter of each capillary per second.

16. Apparatus according to claim 1 wherein the plurality of capillaries is a first set of capillaries and wherein the housing comprises multiple sets of capillaries through which the reaction fluid must flow.

17. Apparatus according to claim 1 further comprising a flow inducer for inducing flow of the reaction fluid through the flow path.

18. Apparatus according to claim 17 wherein the flow inducer provides pressure pulses to the fluid in the flow path.

19. Apparatus for use in performing the steps of PCR melting, primer attachment and reconstruction for replicating DNA located in a polymerase chain reaction (PCR) fluid, the apparatus comprising:

a housing having a flow path through which the reaction fluid may flow, the flow path including a set of reaction chambers comprising a plurality of capillaries into which fluid flowing through the flow path is divided to flow simultaneously before being recombined, such that a flow rate of the reaction solution through the parallel capillaries is lower than elsewhere in the flow path;

heating elements adjacent to the fluid path to change the reaction solution temperature from the primer attachment temperature to the temperatures for PCR reconstruction and melting; and gaseous, liquid or solid cooling means that can be brought into thermal contact with the flow path to reduce the temperature of the reaction solution in the flow path.

20. Apparatus according to claim 19, wherein the flow path is formed, at least in part, by a surface that is thinner than one millimeter.

21. Apparatus according to claim 19, wherein a portion of the flow path comprises a single, convoluted capillary.

22. Apparatus according to claim 19 wherein the plurality of capillaries is a first set of capillaries and wherein the housing comprises multiple sets of capillaries through which the reaction fluid must flow.

* * * * *